United States Patent [19]

Nelson et al.

[11] Patent Number: 4,676,611

[45] Date of Patent: Jun. 30, 1987

[54] METHOD AND APPARATUS FOR VISUAL-EVOKED RESPONSES

[75] Inventors: Jeremiah Nelson, St. James; Mark J. Kupersmith, New York, both of N.Y.

[73] Assignee: New York University, New York, N.Y.

[21] Appl. No.: 671,474

[22] Filed: Nov. 14, 1984

[51] Int. Cl.[4] ............................ A61B 3/10; A61B 3/02
[52] U.S. Cl. ..................................... 351/205; 351/211; 351/243
[58] Field of Search ............... 351/205, 225, 238, 211, 351/243

[56] References Cited

U.S. PATENT DOCUMENTS 4,493,539 1/1985 Cannon ............................... 351/205

Primary Examiner—Rodney B. Bovernick

Attorney, Agent, or Firm—Rosen, Dainow & Jacobs

[57] ABSTRACT

In an apparatus for assessing visually-evoked response, wherein stimulus means are provided to present a variable visual pattern to an observer and analyzing means are provided to analyze scalp potentials of the observer responsive to said pattern; the improvement wherein the stimulus means comprise means for temporal modulation of the pattern at a determined rate and simultaneously sweeping another visual parameter, in a determined period, in a range which crosses an observer's visual threshold for said other parameter, said analyzing means comprising means for synchronously demodulating said scalp potentials employing said determined rate of the temporal modulation as a reference, at a plurality of different phases with respect to said reference, for producing a display of the scalp potentials demodulated with different phase reference.

13 Claims, 11 Drawing Figures

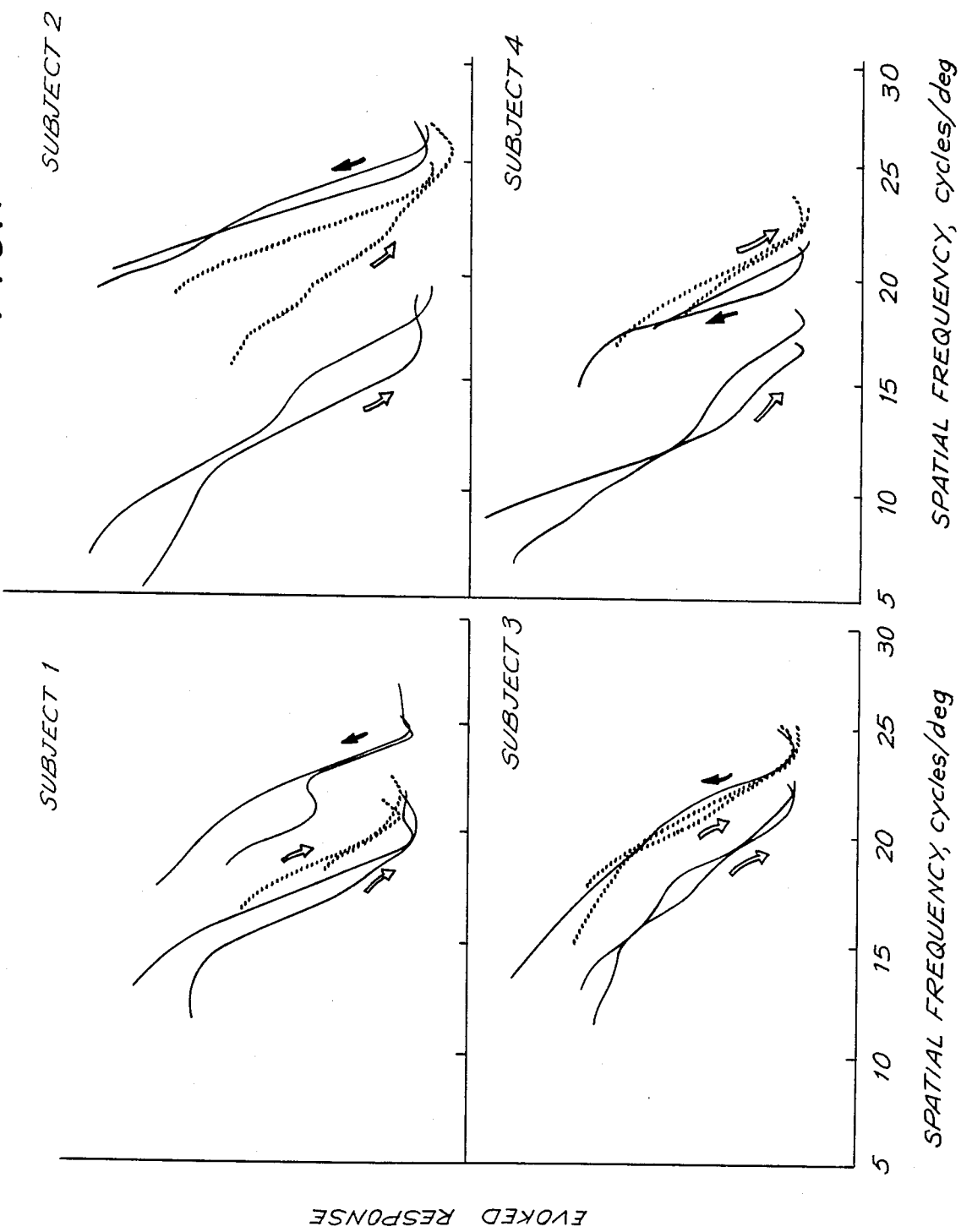

CONTRAST THRESHOLDS IN MULTIPLE SCLEROSIS:
SELECTIVE LOSS BY EYE, ORIENTATION & SPATIAL FREQUENCY

METHOD AND APPARATUS FOR VISUAL-EVOKED RESPONSES

This invention was made with Government support under grant EY 02179 awarded by the National Eye Institute, National Institutes of Health and under grant MH 34793 awarded by the National Institute of Mental Health, Alcohol, Drug Abuse and Mental Health Administration. The Government has certain rights in this invention.

This invention relates to methods and apparatus for visual-evoked response, and is in particular directed to improvements in the method and apparatus for evoking visual response, as well as methods and apparatus for assessing such response.

It is known to study visual characteristics by presenting patterned light stimuli to an observer, and observing the resulting visual-evoked potentials, i.e., to obtain a visually evoked response. Such response has been reported, for example, in "Rapid Objective Refraction Using Evoked-brain Potentials", D. Regan, Investigative Ophthalmology and Visual Science, 1973, volume 12, pages 669–679; "Colour Coding of Pattern Responses in Man Investigated by Evoked Potential Feedback and Direct Plot Techniques", D. Regan, Vision Res., 1975, volume 15, pages 175–183; "Rapid Assessment of Visual Function: an Electronic Sweep Technique for the Pattern Visual Evoked Potential", C. W. Tyler, et al, Investigative Ophthalmology and Visual Science, 1979, Volume 18, pages 703–713; U.S. Pat. No. 3,910,690, Regan and U.S. Pat. No. 4,012,128, Regan.

The essence of any visual evoked response technique lies in stimulus retrieval and the response presentation. Stimulus retrieval had commonly been effected by computer averaging. Averaging requires repeated presentations of the same stimulus and consequently is slow. The averaging technique also causes problems such as the inherent adaptation of the person who is looking at the stimulus. In one improvement over such common averaging practice, the signal is retrieved in real time. This has the important consequence that, if the response is being retrieved as it occurs, then it is possible to change the stimulation in order to evaluate the impact thereof on the response. With this technique, the stimulation may be electronically swept in the course of a run whose duration need only be, for example, 20 seconds.

The apparatus employed for assessment of visual performance may be generally comprised of a display, such as a television screen, upon which a pattern is presented. Scalp electrodes over visual cortex pick up electrical potentials generated by the neural response to visual stimulation. In order to permit retrieval of the visual-evoked potentials, the pattern is temporally modulated, i.e., the black and white areas of the pattern are changed at a determined rate. The visual-evoked potentials is retrieved by demodulating the scalp potential at the pattern reversal rate. Demodulation is performed by a lock-in amplifier. The signal-to-noise enhancement performed by a lock-in amplifier may be viewed as the result of extreme frequency selectivity.

When a lock-in amplifier in the form of a synchronous demodulator referenced at a single phase is employed, the signal-to-noise ratio is satisfactory, but the phase of the reference is critical. In one solution to the criticality of phase, signals demodulated by references 90° apart are combined, forming "vector retrieval". Vector retrieval, while avoiding the criticality of phase of the reference signal, is undesirably subject to noise.

Different parameters of the visual display, such as spatial frequency, contrast, orientation, and reversal or temporal modulation rate can be swept electronically. The stimulus value at which the signal level responding to the stimulus falls to zero, or rises from zero, depending upon the sweep direction, is defined as the patient's threshold for the parameter which was swept. The output of a run, i.e., the output in response to sweeping of a given parameter for a determined time such as 20 seconds, is a graphical, complete description of the desired stimulus-response function. In evaluating the threshold, it is thus necessary to assess the relative time of occurrence of the start or end of the response. The criticality of phase of a conventional phase-sensitive detector and the noise sensitivity of vector retrieval, render the determination of threshold difficult. In accordance with a further feature of the invention, in order to evaluate threshold, it has been found that phase sensitive detection at a plurality of reference phases may be employed, the graphical presentation of the outputs of the different phase sensitive detectors generally converging to or diverging from a common threshold value. In a further feature of the invention, it is unnecesary to establish an arbitrary base line for assessment of the runs, the scalp potentials of the patient being observed in the absence of sweeping the determined parameter, and the run being started at a time of low, preferably decreasing, activity. The response starts indicated by the rise of activity, when the stimulation is made to increase in strength, quite reliably indicate the threshold.

In a still further feature of the invention, combinations of runs are evaluated, with some of the runs starting with the swept parameter below threshold value, sweeping upwardly, and others of the runs sweeping downwardly toward the threshold value. With such tests it has been found that the threshold values differ, depending upon the direction of the sweep. The differences are not attributable to machine error, but, instead, in accordance with the invention, constitute a further evaluatable parameter, i.e., adaptation.

In a still further feature of the invention, it has been found that, by also sweeping the temporal modulation rate or reversal rate of the pattern during a run, the further evaluatable parameter of latency can be measured. Such measurements, when run over very broad swept temporal modulation rate ranges, provide a measure of response frequency spectrum of the individual to the stimulus. This measure permits the selection of stimulus frequencies which produce the highest responses or the lowest noise. In view of the criticality of reference phase in phase sensitive detectors, and in view of the sweeping reference rate, it has been found that phase-sensitive detectors in themselves are unsatisfactory for indicating latency. In accordance with the invention, signals for assessing latency or response frequency spectrum may be derived by vector retrieval methods.

In order that the invention may be more clearly understood, it will now be disclosed in greater detail with reference to the accompanying drawing wherein:

FIG. 7 is a graph illustrating acuity limit inferred from visual evoked response to swept spatial frequency stimulation for four subjects and its alteration by adaptation.

Figure 1:
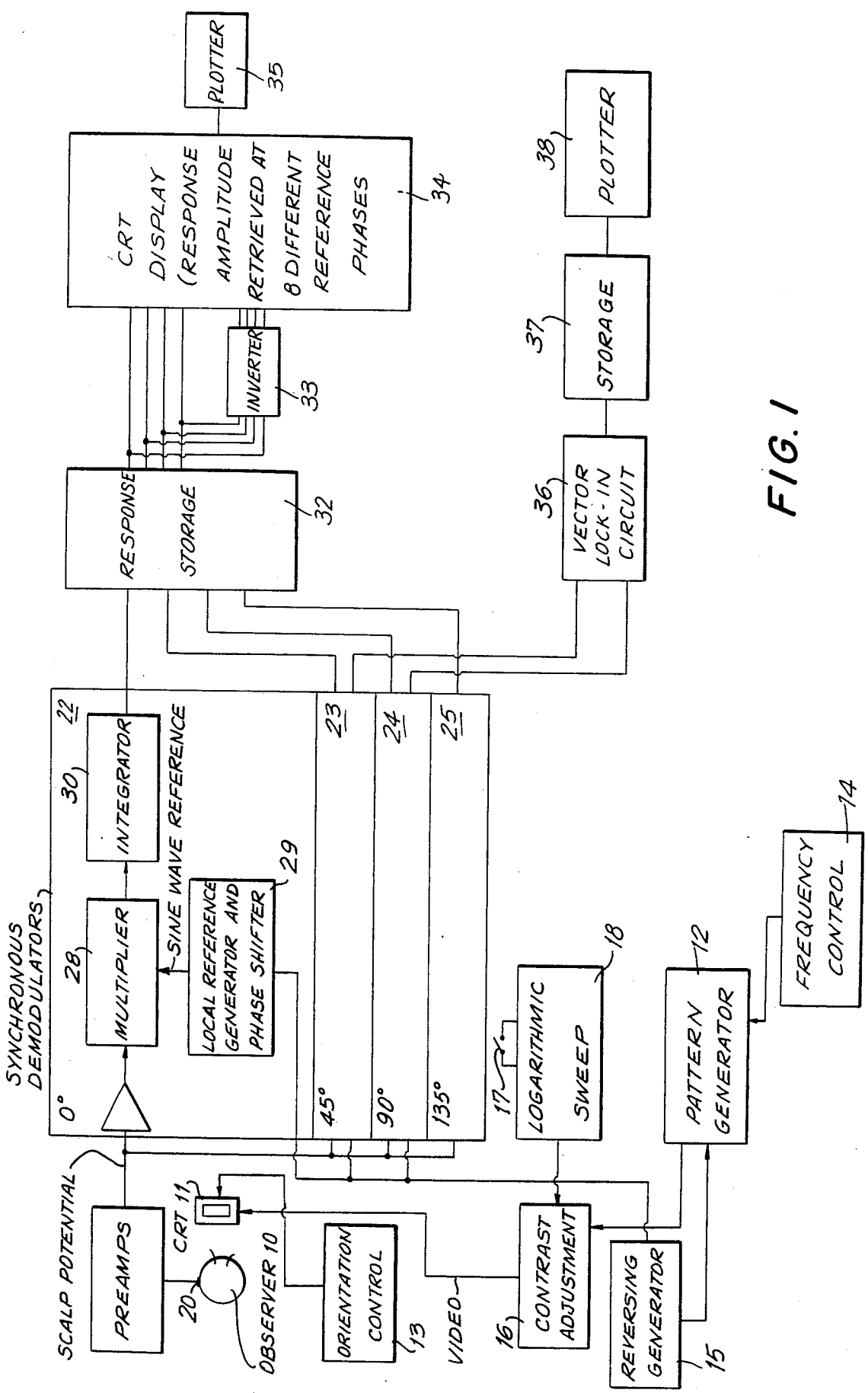
FIG. 1 is a block diagram for visual-evoked response evaluation, in accordance with one embodiment of the invention (contrast sweep)

In order to facilitate the understanding of the invention, one form of apparatus that may be employed in accordance with the invention will first be described with reference to FIG. 1. As illustrated in FIG. 1, a patient or observer 10 is positioned to view the presentation on the screen of a CRT, the screen of the CRT being scanned, for example, in conventional manner, to form a raster. Video signals for application to the CRT are derived from a pattern generator 12, of conventional form. While the pattern generator may generate a checkerboard pattern for application to the CRT, it is preferred that a bar pattern generator be provided, preferably also with the provision of orientation control 13 enabling the orientation of the bars of the screen to be varied, as an example, the orientation control may be adapted to enable the display of the bars vertically, horizontally, and at each 45° orientation with respect to the vertical and horizontal. The frequency of the pattern generator, i.e., the cycles of the pattern per degree of arc of the observer's vision, may be varied by a frequency control 14. As an example, in one embodiment of the invention, tests are made with the frequency of a bar pattern at 1, 4 and 8 bars per degree of the visual arc of the observer. In order to facilitate the demodulation of signals, for example to remove noise, the displayed pattern is temporally modulated at a determined rate. For this purpose, a reversal generator 15 is provided to control the reversal rate of the pattern.

As a still further control of the video signals, the pattern generator video signals may be varied in amplitude (display contrast) by means of a contrast adjustment device 16, for example a gain controlled amplifier. Prior to a test run, the contrast of the signals is held constant, while during one method of operation, the contrast is varied preferably logarithmically from, for example, 0.1% to 20% contrast. For this purpose, a logarithmic contrast sweep circuit 18 is provided to control the contrast adjustment device 16, the sweep being initiated by means of a switch 17.

The development of the video signal as above diagramatically discussed may be effected by any conventional function generation circuits.

As further illustrated in FIG. 1, EEG electrodes 20 applied in conventional manner to the observer's scalp are connected to a pre-amplifier 21, the output of the pre-amplifier being applied to synchronous demodulators 22, 23, 24 and 25. A reference signal from the pattern generator 12, at the frequency of the reversing generator 15, is also applied to each of the synchronous modulators.

It is illustrated in FIG. 1, the input scalp potential applied to synchronous modulator 22 is amplified and applied to a multiplier 28. The reference signal from the pattern generator is applied to a local reference signal generator and phase shifter 29 for the generation of a sine wave reference signal having a phase of zero degrees with reference to the reversing generator signal. The output of the local reference generator and phase shifter 29 is applied to the multiplier 28 as a reference signal, with the output thereof being integrated in integrator circuit. The synchronous demodulator 22 hence comprises a phase sensitive detector. Each of the synchronous demodulators 23, 24 and 25 are constructed in a similar manner, with the exception that the respective local reference generators and phase shifters provide sine wave reference outputs at 45°, 90°, and 135° respectively with reference to the reversing generator output. The outputs of the synchronous demodulators are applied to a response storage 32, for example a digital storage device, for storing the received signals over a given period of time (the sweep time). The four outputs of the response storage 32, corresponding to the input thereto, are each applied directly and by way of an invertor 33 to a CRT display 34, the output of the CRT display may apply, if desired, to a conventional plotter 35.

In addition the outputs of two of the synchronous modulators 22-25 that are displaced by 90°, for example, the synchronous modulators 23 and 25 are applied to a vector lock-in circuit 36. The vector lock-in circuit 36, in the embodiment of FIG. 1, combines the two input signals employing analog computational circuitry, (1) in a root mean square algorithm, and (2) an arctangent algorithm. These signals may be stored in storage device 37, such as a digital memory, and applied to a conventional plotter 38.

Briefly stated, in the use of visual evoked response equipment such as provided in the invention, a varying optical pattern is applied to the screen of the CRT, for a determined period of time, preferably although not limited to 20 seconds, and the scalp potentials received during this period are analyzed, in order to enable assessment of the response of the observer. The varying visual pattern may constitute, for example, a swept contrast or a swept spatial frequency. When contrast is swept, the contrast of the pattern is slowly increased or swept, preferably upwardly from a very weak initial value. Eventually a pattern becomes visible on the screen, and grows from a washed out appearance to a vividly distinct appearance. Simultaneously, the evoked potential amplitude, i.e., the scalp potential responding to the stimulus, climbs. The point at which the response first appears defines an absolute contrast threshold for the particular pattern chosen. When the pattern is a swept spatial frequency pattern, an analagous sweep in spatial frequency might proceeds from coarse gratings to stripes too fine to resolve. The point at which evoked response disappears defines an acuity limit. In this case, with a downward sweep, the response strength falls to the threshold value. Upward sweeps, however are always preferable in clinical practice because of their freedom from adaptation as discussed below.

As an aid to extrapolation, contrast is swept logarithmically with time. This logarithmic transformation of the stimulus input is more nearly a straight line as a function of time. Resolution is also improved since a logarithmic sweep renders contrast changes gradual in the threshold region. While equipment employed may not provide true logarithmic functions, it has been found that imperfect linearization does not impair threshold determination.

Spatial frequency sweeps, on the other hand, are preferably performed linearly with time, since human pattern sensitivity is itself a logarithmic function of spatial frequency near the acuity limit. The stimulus response function describes the amount of evoked response in micro volts elicited when presenting stimuli of varying strength, measured in percent contrast or in grating spatial frequency. When strength is varied by changing spatial frequency, it is only the response fall off at very high spatial frequencies that is of concern. The fall off is used to infer the acuity limit.

Our contrast testing methods describe the observer's contrast sensitivity function. Evoked potential magnitude observed as spatial frequency changes cannot be used as a quick substitute for measuring contrast sensitivity at each of many selected spatial frequencies, since a spatial frequency capable of eliciting a large evoked potential amplitude is not necessarily capable of eliciting a low contrast threshold. In other words, the stimulus-response function for evoked response vs. stimulus contrast is unknown, so that a threshold determination must be made for each particular spatial frequency.

As above discussed, in order to separate the visually evoked response from signals not related to the response, (noise), the visual pattern is modulated by a reference temporal frequency signal that cyclically reverses the pattern at a determined rate. By synchronously demodulating the scalp potential at the frequency of the reversing generator, noise (energy at other frequencies) is substantially eliminated. Since the synchronous demodulators are phase sensitive, their noise immunity is greater than with phase insensitive vector retrieval, of the type provided in the vector lock-in circuit 36. For example, as illustrated in FIGS. 2a and 2b, showing 20 second runs employing spatial frequency variation and contrast variation respectively, the solid curves showing phase sensitive detection response are less influenced by noise than vector retrieved response. In other words, since the vector retrieved response is the function of amplitudes at 90° separated references, signals of all phases are retrieved, and this retrieval has poor noise immunity response. In FIG. 2A, a 75% contrast sine wave grating was modulated at 7 reversals per second and swept in spatial frequency toward the acuity limit. A noise pulse occurring at the time A has distorted the signal output of the vector lock-in circuit, but has not affected the output of the phase sensitive detector. In FIG. 2B, a one-cycle per degree sine wave grating was modulated at three reversals per second and swept in contrast. A noise pulse at time C affected the output of the vector lock-in circuits but not the output of the phase sensitive detectors.

Figure 3:
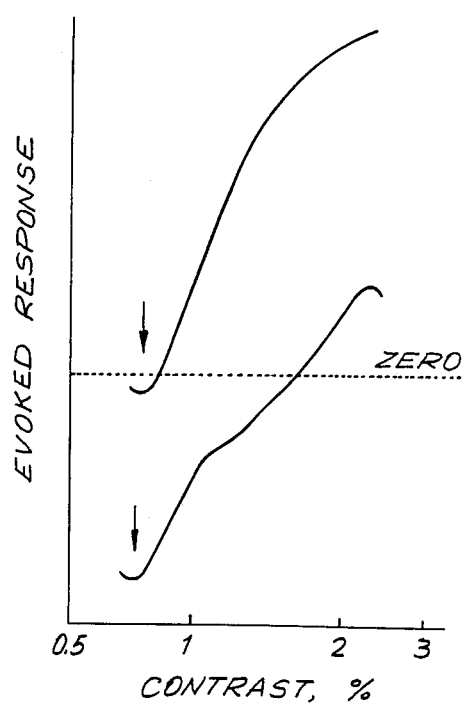
FIG. 3 is a graph illustrating the determination of a base line.

Due to background EEG activity, the outputs of the integrators of the phase-sensitive detectors may be at any of a wide range of positive or negative values with respect to electrical zero, at the time a run, i.e., a test for a determined period of time, is commenced. The visually evoked response is added to a widely displaced starting level. In prior techniques, thresholds had been defined by extrapolation to a base line chosen either at absolute zero voltage or at an average noise level. It has been found, however, that these techniques do not provide a correct response in a biological recording situation. Only if the output level at the beginning of the response is used as a base line, will extrapolation of the response slope yield identical threshold estimates. This is illustrated in FIG. 3, wherein two sweeps of increasing contrast have been made to determine the observer's contrast threshold. Electrical zero is indicated by the dotted line. The two sweeps were purposely done when the integrator had been charged by non-visual EEG activity to two very different starting voltages. It can clearly be seen that the response begins its climb at the same contrast value regardless of the initial charge level on the capacitor of the integrator. The response-start point is indicated by two arrows for the two runs: evaluated in this way, both runs indicate a threshold of about 0.7% contrast. The time at which the visually driven response happens to cross absolute zero voltage does not define a threshold. The zero crossing point occurs at approximately 1.5%. This is implausibly high for contrast thresholds under these conditions, does not agree with the result of the other run, and would vary arbitrarily with arbitrary changes in the choice of initial starting level. In accordance with the invention, it is preferred to first wait for the ongoing activity output of the EEG to drive the output of the phase-sensitive detector channel of interest to a low voltage, thus maximizing the dynamic range available for the response. Then, a trial run is begun when the phase sensitive output detector is stable or falling slightly in amplitude. This may be achieved by electronically discharging the capacitor of the integrator, or waiting for an opportune time in the ongoing EEG. Under these conditions, a well defined starting point or turn-around point will occur when the response commences, identifying both the starting time and the starting voltage level.

Figure 2:
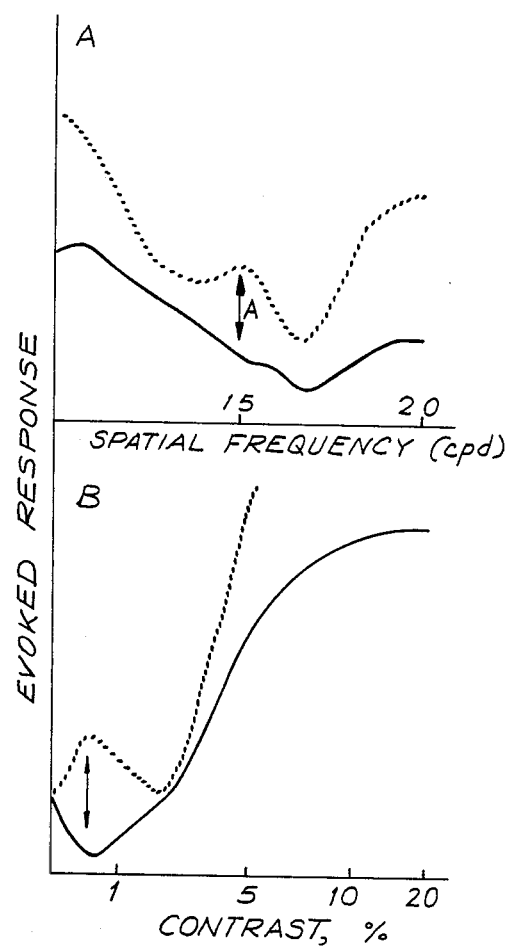
FIG. 2 is a graph illustrating typical spatial frequency and contrast responses, and the superior noise immunity of phase sensitive detection in comparison to vector retrieval.
Figure 4:
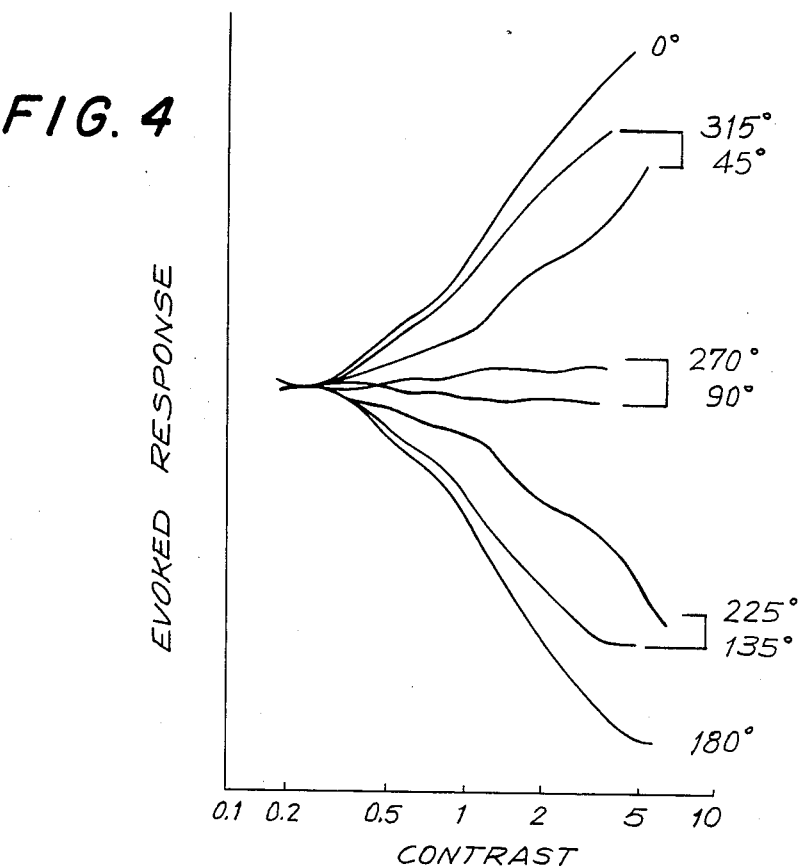
FIG. 4 is a graph illustrating the combination of phase-sensitive detector outputs at different reference phases, for determining the threshold values.

If vector retrieval is employed in the determination of the threshold, as a result of the lack of noise immunity of such retrieval, as depicted in FIG. 2, it is apparent that the indication of threshold may be incorrect. If, on the other hand, a single phase-sensitive detector is employed to determine threshold, the selection of the phase of the reference signal is critical. In accordance with the present invention, however, by employing a plurality of phase-sensitive detectors set to detect at different phases, the reference phase is no longer critical. For example, if the reference phase is 180° from the optimal phase, response is inverted but still retains the maximum amplitude (slope) and indicates the same threshold. As illustrated in FIG. 4, all other angles than the optimal (in this case 0° and 180° from the optimal), reduce the slope of the visually evoked response function but do not change the threshold, i.e., the contrast (or frequency) at which the response starts to rise or fall. It is thus apparent that the responses of a given run as stored in the response storage 32 of FIG. 1, provide, in combination with the inverter 33, data for the display of 8 different reference phases as illustrated in FIG. 4. Since the response detected at each of the reference phases commences a rise or fall at the same point, it is apparent that this point represents the threshold contrast or frequency.

Considering initially variations in contrast, it has been found that output on upward and downward sweeps of contrast, i.e., from indistinguishable to distinguishable and vice versa, are not symmetrical. Threshold depends upon delay to start in one case, and on delay to finish in the other case. In practice, there are conditions when thresholds determined in runs of decreasing stimulus strength (downward sweeps) will be either apparently more sensitive than, equal to, or apparently less sensitive than upward thresholds. These conditions are considered in turn as follows:

(1) Downward thresholds will be erroneously lower when the rate of change of the visually driven response exceeds the maximum rate of change of the instrument. Under these conditions, response tracking cannot occur, and output slope is limited by its time constant. Under such conditions the response may have ended, but the instrument cannot discharge rapidly enough to indicate this. By the time threshold is indicated, the stimulus is much fainter and it can be erroneously inferred the subject is more sensitive. Threshold inferred from upward sweeps are free of this problem. A difference between the two sweeps constitutes an instrumental artifact under these conditions.

(2) If the slope is not limited by time constast of the instrumentation, the instrument tracks the response and thresholds inferred on up and downward sweeps will ideally be equal.

(3) In practice, thresholds for contrast inferred from downward sweeps are usually elevated. It is as if the instrument is not only tracking the response, it is getting ahead of itself. Such a negative delay is technically impossible; it cannot arise from instrumental factors. Instrument delay is more likely to occur where large contrast changes executed in a short time require rapid response changes to be tracked. We attempted to convert the puzzling threshold elevation to a threshold depression by sweeping contrast over a 70% range in 20 seconds. In the threshold region, the logrithmic sweep produces a 4.5% contrast change in 7 seconds. The threshold elevation was diminished but still persisted. Condition 1 (artifact) is not occurring; instead, the threshold elevation must be biological in origin. This technique hence provides a means of inducing cortical neural adaptation and measuring it with the visual evoked response. Adaptation appears to occur on downward sweeps because the subject views suprathreshold contrast prior to his threshold determination. Visual-evoked response inferred thresholds can be elevated under such circumstances.

Figure 5:
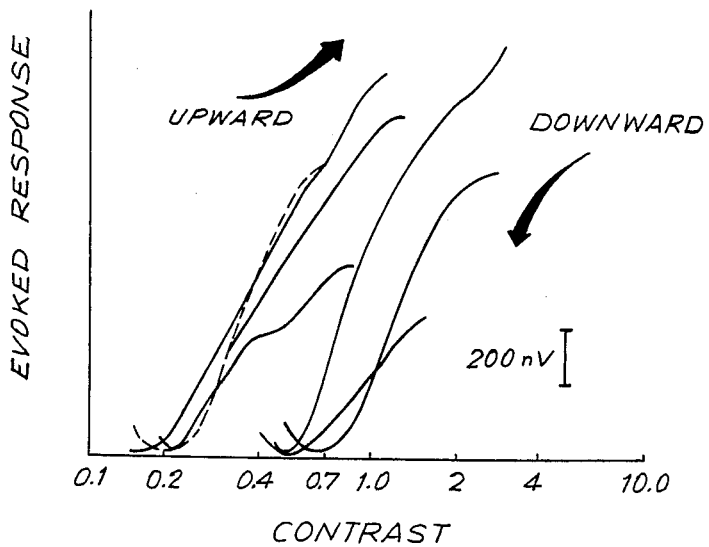
FIG. 5 is an illustration of adaptation effects in visual-evoked response inferred thresholds.

Adaptation effects are illustrated in FIG. 5, showing the visual-evoked response thresholds. In the runs of FIG. 5, stripes ½ degree on a side were modulated at 7 reversals per second and swept either upward in contrast or downward, these runs being shown in solid lines. Sweeping upward from a subthreshold contrast produced lower inferred contrast thresholds and sweeping downward. (Instrumental delay artifacts would cause the opposite difference). Threshold was restored for a downward contrast sweep when the pattern was continuously rotated during the run (as illustrated in the dashed line). This indicates that an orientation-specific adaptation effect causes threshold elevations whenever contrast is swept downward from high values. Orientation selectivity suggests a cortical origin for the effect.

For downward sweeps the stimulus-sweep speed should be adjusted with respect to the chosen instrument time constant so that the instrument will track the true response slope. Under these conditions the dominant factor in up/down threshold differences is adaptation. This is especially true for sweep paradigms in which the spatial configuration of the stimulus is constant. The difference in thresholds inferred from an upward and a downward sweep of contrast provides a direct, objective, electrophysiological index of adaptation.

Threshold differences are seen because "Upward" and "Downward" sweeps provide different opportunities for adaptation. An upward sweep is defined in terms of strength of the stimulation; here, an upward sweep was always begun with subthreshold values (low contrast or unresolvably high spatial frequencies for contrast and acquity limit runs respectively). Thus, on an upward sweep, the subject had no prior exposure to the stimulus at the moment threshold is determined. In contrast, on downward sweeps there is a continuous exposure until threshold is reached. The difference inferred threshold between an upward and downward sweep may be used as an index of adaptation.

Prior exposure to a high contrast grating lessens sensitivity to subsequently presented targets. Such contrast threshold elevation is selective for stimulus dimensions such as orientation and spatial frequency. The selectivity function has been employed in psychophysical research to define "channels" in the human visual system thought to be related to findings at the cellular level in neurophysiology. The present invention provides a technique and apparatus rendering it possible to express cortical adaptation as a threshold elevation measurement employing evoked potential responses. Induction of adaptation and assessment of threshold elevation are economically combined in a pair of 20-second data collection periods. It has been demonstrated in accordance with the invention that reliable threshold displacements occur on upward versus downward sweeps of stimulus intensity.

Figure 6:
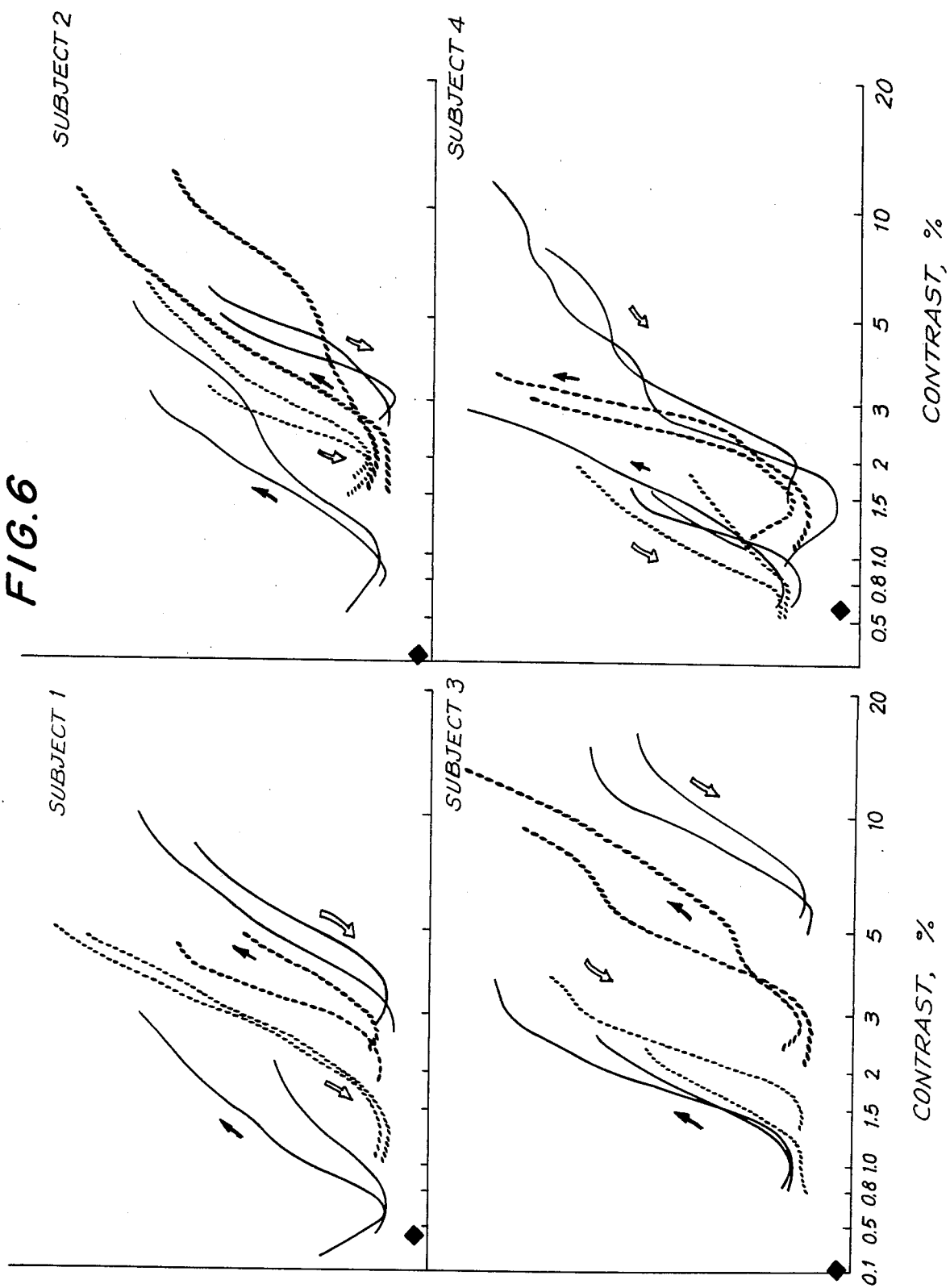
FIG. 6 is a further graph illustrating adaptation effects in the contrast thresholds inferred from the evoked potentials for four subjects.

The visual-evoked response index of adaptation for swept contrasts for four individuals is illustrated in FIG. 6, wherein each of the separate graph portions correspond to a separate individual. Responses indicated by solid arrows were swept from below threshold (0.1%) to 20% contrast, while responses indicated by the outline arrows began at 20% contrast and swept downwardly toward threshold. In each case it is apparent that the downward swept runs showed higher threshold levels than the upward swept runs. The solid lines in the left of each graph correspond to runs in which contrast increased with time, and the solid lines to the right of each graph, having the highest thresholds, correspond to runs in which the contrast decreased with time. The dotted lines show the response with contrast decreasing with time, and, as opposed to the other runs, with the grating constantly rotated at approximately 6 revolutions per minute. The broken lines correspond to visual-evoked response with contrast increasing with time, but wherein the subject was pre adapted for one minute to 75% contrast grating of the same orientation and spatial frequency.

When swept spatial frequency is employed, superior acuity limits are always obtained when the spatial frequency response is swept upward in strength, using stripes initially too fine to be resolved, as illustrated in FIG. 7. In the spatial frequency swept runs of FIG. 7, the solid lines to the left of each graph show stimulus and response strength decreasing with time from values at which they are strongly adapting. The solid lines to the right of the graph were obtained with the response strength increasing with time, these runs illustrating the best thresholds. The dotted lines illustrate the evoked response with decreasing stimulus sweep, with the grating constantly rotated at apppoximately 6 seconds per revolution.

To summarize, threshold differences arise when visual-evoked potential inferred contrast sensitivity is obtained from runs in which contrast is either increased in time from a negligible starting value, or decreased toward threshold from a high contrast value. Similar smaller differences occur for upward and downward swept frequency runs. Each of these differences is an index of cortical adaptation. The adaptation index depends upon separating technical from biological causes of apparent threshold shifts observed in swept stimulus experiments. In considering delays with the instrumentation, it is important to draw the distinction between the time required for the instrument's integrator to begin charging, and the time required for it to assymptotically approach its final value. The time to begin to begin charging is the significant one for determining the start of the evoked response, which in turn determines the inferred threshold. This delay is ideally zero; in practice, the delay is 0.9 seconds. The delay in either sweep direction is constant, however, and works against the reported effects. With delay on a downward sweep for example, spatial frequency will have progressed to finer stripes in contrast to lower values before the instrument is able to indicate that threshold has been reached. In spite of this, it has been found that threshold is elevated. Consequently, this elevation must be biological in origin. The differences in visual-evoked potential inferred thresholds with up and downward swept displays thus reflects visual systems properties.

Orientation selectivity in the geniculocortical pathway prior to striate cortex is mild, in part dependent on cortical downfeed, and occurs as a slight modulation in excitability, not a sharp response flanked by silencing inhibition, as in the cortex. The cortex is also the site for sharp and varied spatial frequency selectivity. Spatial frequency optima differences at a given retinal eccentricity are due primarily to the presence of WXY ganglion cell classes. As each class has different central destinations and functional specializations, these retinal-level tuning differences are unlikely to be the basis for discrimination of spatial frequencies in one visual field locus or one cortical projection area. The threshold shift is sharply orientation and spatial frequency selective (see FIGS. 6 & 7 dotted line downward sweeps). The threshold shifts therefore are believed to be a selective adaptation effect of cortical origin. The swept technique in accordance with the invention hence emerges as an effective means both inducing and quantitatively measuring large threshold elevation after effects. Threshold difference between up and downward sweeps provides a convenient, rapid, objective index or cortical adaptation which is electrophysiologically and psychophysically interpretable.

With swept visual-evoked potential techniques, routine visual assessment is preferably performed with stimulus strength programmed to go upward from threshold, not downward toward it. Because it uses a single presentation of a stimulation beginning below threshold, the upward swept display technique offers an advantage in giving more accurate, less adapted thresholds.

The adaptation effect is somewhat smaller with acuity limit (spatial frequency) sweeps than with contrast threshold determinations. This is attributable to changes in spatial frequency of over two octaves inherent in these acuity runs. Because the adaptation effect originates in the visual cortex where neurons are spatial-frequency selective, responses will be evoked from previously unstimulated spatial frequency channels as the test sweep progresses. These unstimulated channels are not adapted. Threshold improvement of downward sweeps (strong stimulus initially) with added stimulus orientation is more complete for acuity limit than for contrast threshold determinations. This must be due in part to the fact that the two stimulus dimensions are being swept to previously unseen values.

The main reason for the sensitivity of this technique appears to be the lack of delay; even a few miliseconds permit significant amounts of pattern adaptation to leak away. For contrast threshold elevation in particular, there is dissipation of adaptation, not storage, unless the subject is placed in complete darkness between induction and test. With the visual-evoked potential and upward sweeps, threshold is fixed the instant a stimulus appears, although the remainder of the response function helps to identify and confirm the threshold point. On downward sweeps, a supra threshold stimulus is present to produce adaptation until the instant of threshold determination.

The practical significance of these results for visual assessment with visual evoked potential is clear; thresholds inferred from a series of computer averaged responses must typically be adapted thresholds, due to repeated supra-threshold stimulation. Indeed, when special methods are employed to resolve individual sweeps, amplitude decreases may be seen in the discrete evoked potential following the initial presentation of the stimulus. Recent psychophysical research shows longer buildup and recovery times for contrast adaptation than previously supposed, so that brief testing sessions are advantageous. The present invention can eliminate or measure adaptation effects in the visual evoked potential as desired.

It is known that acuity and contrast thresholds vary slightly with stimulus orientation. Sensitivity is superior for horizontal and vertical orientations. This is termed the oblique effect. The present methods are capable of detecting these small differences in threshold. It is known that there are at least two fiber systems from retina to cortex, termed X and Y systems, that the X system responds preferentially to low temporal and high spatial frequencies and conversely for the Y system, and that the X system has oblique effect properties and the Y system does not.

Under spatial temporal conditions which abolished the oblique effect, inferred contrast thresholds were somewhat lower and acuity thresholds were considerably higher than under spatial temporal conditions which supported an oblique effect. These observations suggest that threshold behavior can be determined by different mechanisms as spatial temporal conditions are varied. The variation from fine to coarse spatial frequency may bring a shift between what have been termed the pattern versus luminance components of the evoked potential, because even coarser spatial frequencies do present local luminance changes to ever larger retinal areas. In a way, separate XY visual subsistance are expected to underly these evoked potential components and visual performance differences. Evidence indicates to the identification of potentials evoked at temporal frequencies of three reversals per second or below and spatial frequencies of 4 cycles per degree or above with an X-dominated generator and to potentials at 43 Hz or one cycle per degree and any reversal rate down at least to 3 reversals per second with a Y-dominated generator.

Using cortical visual evoked potentials in man, in accordance with the present invention it has been shown that the oblique effect can be elicited with low temporal frequencies and high spatial frequencies, while rapid reversal rate or low spatial frequencies are each alone sufficient to abolish it. The presence of the oblique effect is a marker for an X-dominated scalp potential; when the oblique effect is abolished, the scalp potential is Y-dominated. In this further utility of the invention, the provision of threshold-level and adaptation-free responses separate, and non-invasively test, the performance of X and Y retinocortical pathways.

Figure 8A:
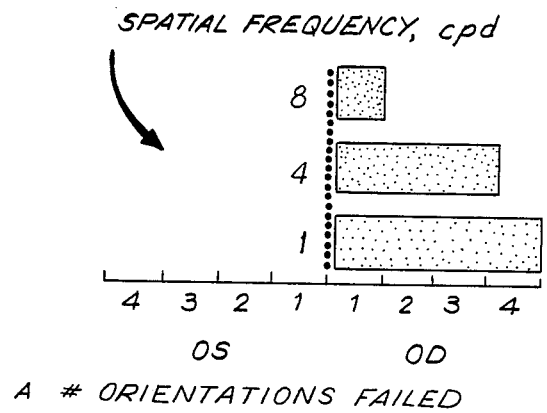
FIG. 8A is a graph illustrating a key to the interpretation of FIG. 8B.

The visual evoked response has been shown to demonstrate differences in visual function of patients, indicating the value of visual evoked response employing the techniques and apparatus of the present invention in diagnosis. Thus, it is known that multiple sclerosis can produce highly selective losses in visual function. The selective nature of the losses make them hard to find, and exhaustive testing has heretofore been necessary. In one example, in accordance with the invention, 15 cases of patients having probable or definite multiple sclerosis were studied. Ten persons having no history of opthalmological, biological or neurological disease served as controls. FIG. 8A illustrates the key to the schematization, OS referring to the left eye and OD referring to the right eye. Tests were made employing contrast thresholds, at each of the spatial frequencies 1,4 and 8 cycles per degree, as indicated by the lower, middle and upper bars. These bars have lengths corresponding to the number of orientations wherein abnormally high contrast thresholds were observed. In the controls, no such abnormalities appeared. FIG. 8A only shows the responses for the right eye, it being apparent that similar responses are provided for the left eye.

Figure 8B:
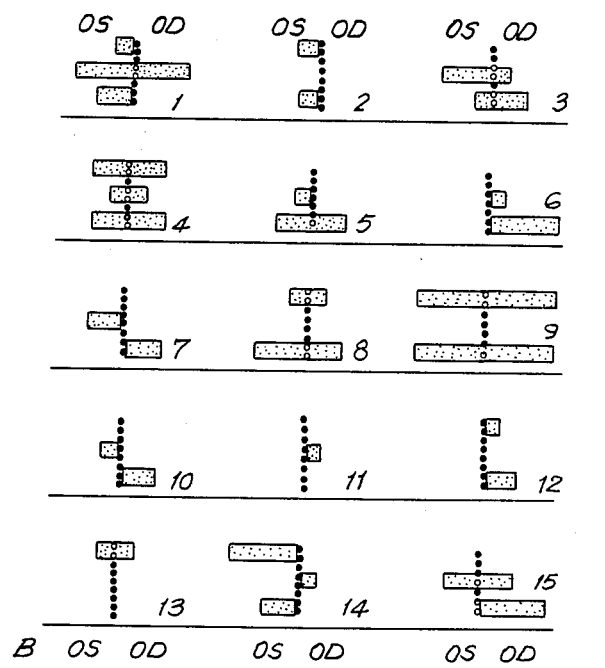
FIG. 8B is a draft illustrating test results at 3 spatial frequencies for 15 multiple sclerosis patients.

FIG. 8B illustrates the responses of the 15 cases, each graph showing abnormally high contrast of thresholds in at least one orientation and in at least one eye (X indicates that a parameter was not tested). This is a higher diagnostic yield than with any other clinical testing method.

Contrast sensitivity can hence be measured, in accordance with the invention, reliably in a clinical setting with swept visual evoked response. The test is rapid enough to permit testing of several orientation and spatial-frequency values in each eye separately.

Figure 9:
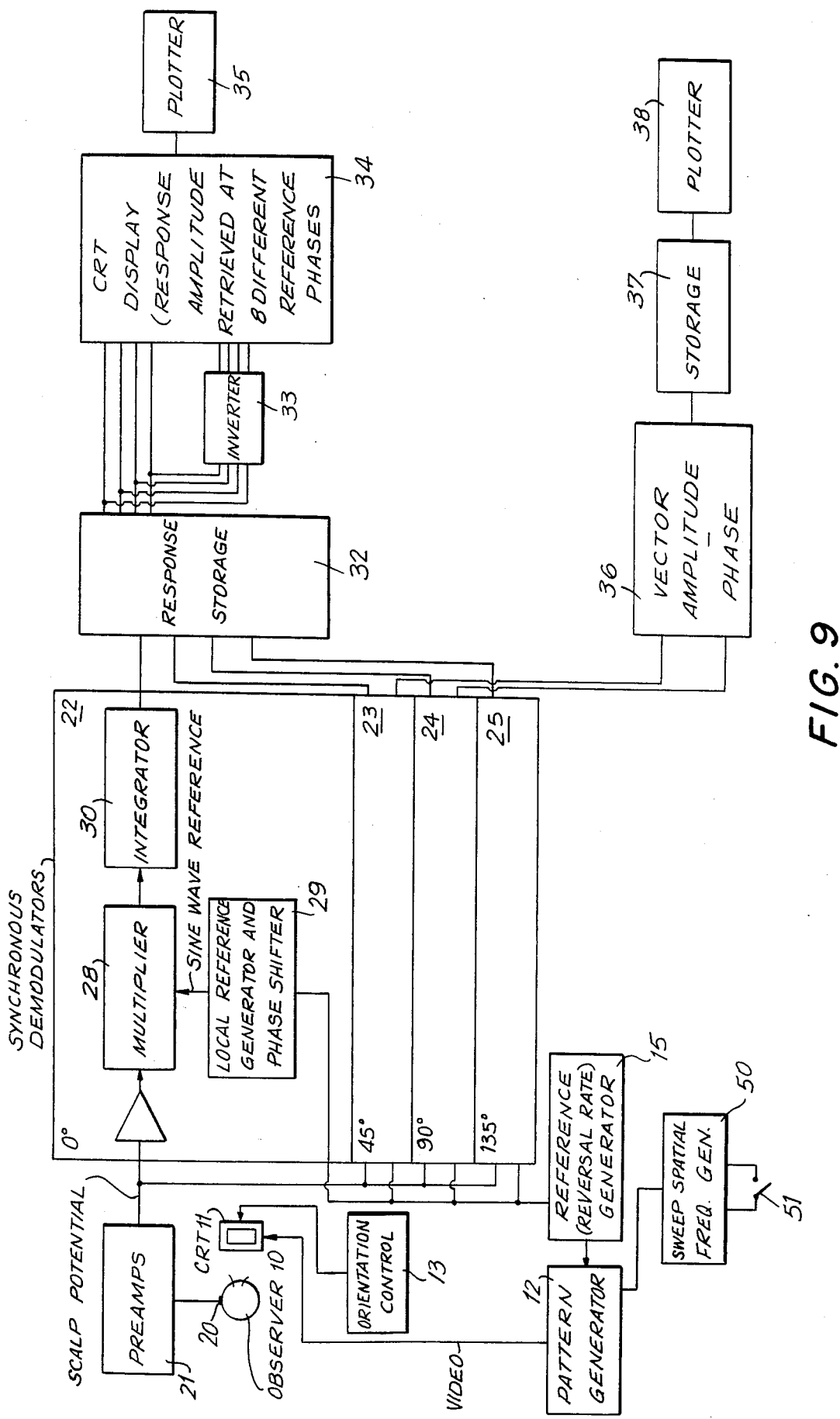
FIG. 9 is a block diagram illustrating a modification of the circuit of FIG. 1 (spatial frequency sweep)

As discussed above, tests may be made sweeping the contrast of the display, for example employing the apparatus of FIG. 1, or the spatial frequency of the pattern (for example cycles of a bar pattern per degree of visual arc of the observer) may be swept. For this latter purpose, a circuit such as disclosed in FIG. 9 may be employed, wherein the pattern generator 12 is controlled in spatial frequency by a ramp generator 50 adapted to cause either upwardly or downwardly ramping spatial frequency (cycles of the pattern per degree of visual arc) as desired. The start of a run may be effected by means of a switch 51 connected to the ramp generator, in order to commence the run at a low EEG activity level, as discussed above.

Figure 10:
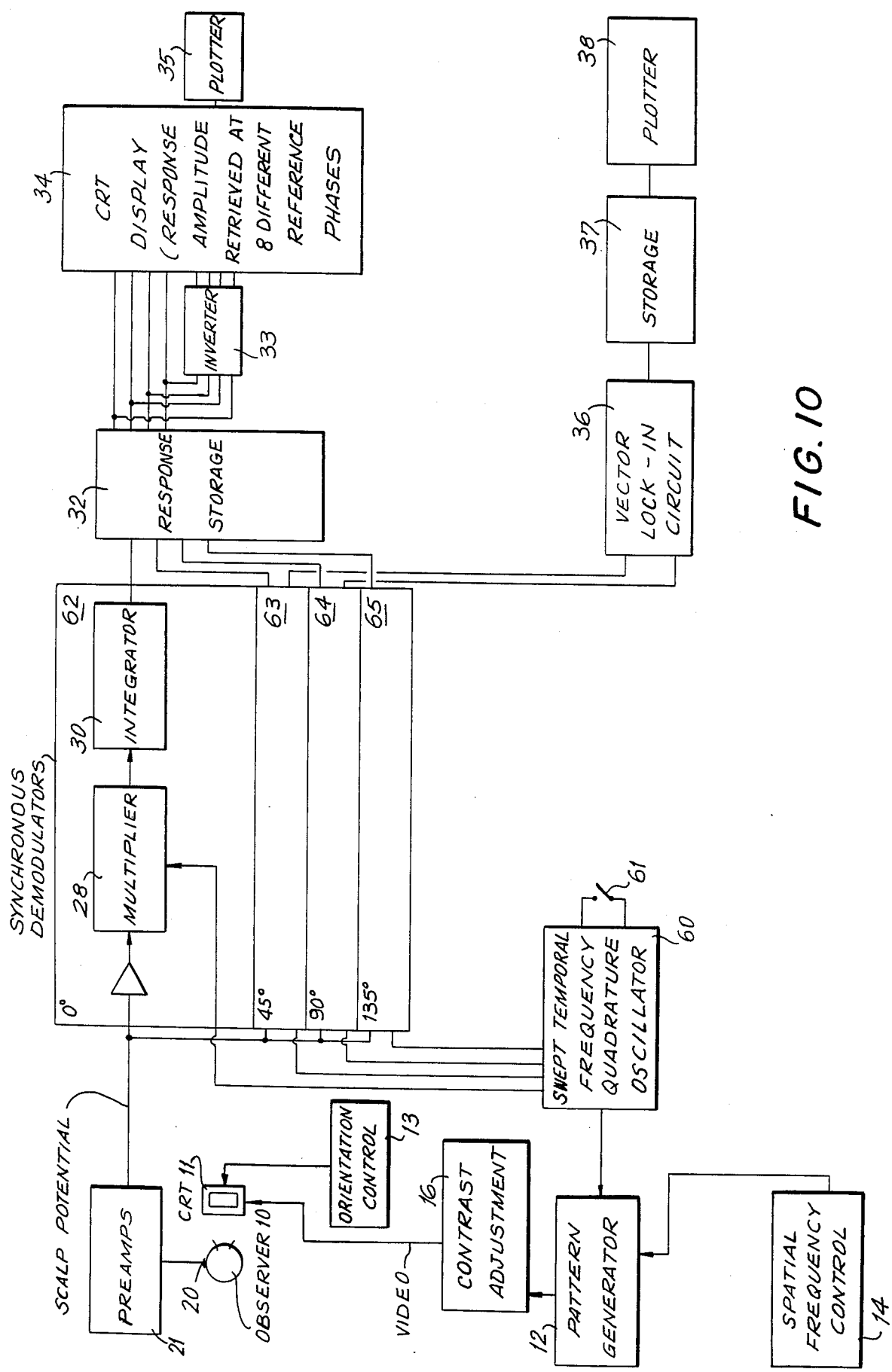
FIG. 10 is a block diagram illustrating a still further modification of the circuit of FIG. 1 (temporal frequency sweep).

In a further embodiment of the invention, as illustrated in FIG. 10, instead of employing a constant reversal rate in referenced generator, the reversal rate is swept in frequency, by means of swept frequency quadrature oscillator 60. Since it is not feasible, in this case, to employ a local reference generator and phase shifter in the sychronous demodulators 62–65, in view of the inability of such local generation to properly follow the reference, the swept frequency quadrature generator 60 also provides output reference signals at zero degrees, 45 degrees, 90 degrees and 135 degrees, for application to the multipliers 28 of the synchronous modulators. In the arrangement of FIG. 11, the sweep of the frequency of reversals is commenced by means of the switch 61.

Thus, in accordance with the invention, the reversal rate itself can become a dimension of interest rather than merely a reference signal for the synchronous modulation. This technique provides a measure of latency. Latency is a measure of the time it takes for a response to go from the visual input to the eye to an observable electrical activity in the scalp potential.

In prior visually evoked response techniques, employing computer averaging, a discrete stimulus was applied, and the delay in the response constituted a measure of latency. Since a single response could not be seen, it was necessary to repeat the test, for example, 128 times, in order to obtain a measureable potential. From an engineering point of view, looking at the temporal modulation continuum, i.e., the frequency spectrum, prior techniques measure one point on the frequency spectrum. This is the latency at a very low temporal frequency.

In accordance with the present invention, a sweep of the reversal rate may be varied, for example, from 3 reversals per second to 50 reversals per second or more, during the 20 seconds or the like of the run. The run in this case thereby fully characterizes the temporal transfer function of the system. Latency may be measured at any temporal frequency. Latency measurement at more than one temporal frequency has an important biological utility as well, since the visual pathways can be divided into at least three different pathways which are called the WXY type pathways. The pathways are characterized by many structural and functional differences in which one of the primary structural differences is that the WXY pathways have different fiber diameters, increasing in that order. The larger an axon fiber diameter, the faster is the conduction obtained. The fastest-conducting system is also the most, if not the only, responsive system at high temporal frequencies. There is currently increasing interest in whether different forms of different diseases differentially attack these different pathways.

If a disease is present that affects, for example, the higher speed system, latency is more greatly affected than if the disease is primarily directed to a slow speed system. By the same token, if a disease is present that affects the high speed system, it can be singled out for measurement by looking at the latency at a high temporal reversal rate. Consequently, measurements of latency which can be made at any temporal frequency, enable one, in terms of biological and medical applicability, to separately assess different pathways or different neural populations. The invention enables the measurement of latency in a readily interpretable way, not in terms of wave form, but in terms of understood aspects of visual performance. Thus, by choice of an incisive stimulus and by looking at measurements which can be compared with both the psychophysical and the neurophysiological functions, one can gain insights into disease processes, i.e., the effect of the disease on different pathways. In accordance with the invention, then, the different test runs may be made in different small portions of the total spectrum, for example, from 3 to 13, or 5 to 15, etc. reversals per second. The output of interest in this case is a phase function curve. The slope of the phase line provides a measure of latency.

When runs are made with swept frequency reversal rates, it is apparent that the resultant shifting phase of the reference renders the output of the different synchronous demodulators variable as a function of the instantaneous reference frequency. Accordingly, in accordance with the invention, in order to measure latency, a vector lock-in circuit 36 is employed. Vector lock-in circuits, by taking the ratio of the outputs of two phases demodulated at 90 degrees with respect to one another, are able to calculate phase information as a tangent function. The provision of the vector lock-in circuit 36 hence enables the measurement of latency. In view of its sensitivity to noise, however, vector computation methods are is not generally preferred for the other above discussed measurements.

In the above discussion, periods for the various testing runs has been suggested to be 20 seconds. It is of course apparent that the invention is not limited to this time period.

While the invention has been disclosed and described with reference to a limited number of embodiments, it is apparent that variations and modifications may be made therein. Thus, as discussed above, the time for each run may be varied. Similarly, the ranges of contrast variation, spatial frequency variation, and reversal rate variation may be varied, and other conventional systems may be employed for generating the patterns. It is therefore intended in the following claims to cover each sense of variation and modification as falls within the true spirit and scope of the invention.

What is claimed is:

1. In an apparatus for assessing visually-evoked response, wherein stimulus means are provided to present a variable visual pattern to an observer and analyzing means are provided to analyze scalp potentials of the observer responsive to said pattern; the improvement wherein the stimulus means comprise means for temporal modulation of said pattern at a determined rate and simultaneously sweeping another visual parameter, in a determined period, in a range which crosses an observer's visual threshold for said other parameter, said analyzing means comprising means for synchronously demodulating said scalp potentials employing said determined rate of the temporal modulation as a reference, at a plurality of different phases with respect to said reference, for producing a display of the scalp potentials demodulated with different phase references.

2. The apparatus for assessing visually-evoked response in accordance with claim 1, wherein said analyzing means further comprises means for inverting the output of said means for synchronously demodulating, and means responsive to the inverted and uninverted output of said means for synchronously demodulating for producing said display.

3. The apparatus of claim 1 wherein said visual parameter is contrast, and said means for sweeping said other visual parameter comprises sweeping said contrast from the level of indistinguishable to a level of distinguishable contrast.

4. The apparatus for assessing visually-evoked response of claim 1 wherein said other parameter is acuity, and said means for sweeping said other visual parameter comprises means for sweeping the spatial frequency of said pattern, in cycles of said pattern per degree of visual arc of vision of said observer, from a level at which said pattern is readily visible to a level at which said pattern is not visible to said observer.

5. The apparatus for assessing visually-evoked response of claim 1 wherein said means for synchronously demodulating comprises a plurality of phase-sensitive detectors.

6. In a method for assessing visually-evoked response wherein a variable visual pattern is presented to an observer and the scalp potentials of the observer responding to the stimulus of the variable visual patterns are analyzed; the improvement comprising sweeping a visual parameter of said variable visual pattern, in a predetermined period, in a range which crosses an observer's visual threshold for said parameter, temporally modulating said pattern at a determined rate during said sweeping, synchronously demodulating said scalp potentials employing said determined rate of the temporal modulation as a reference, at a plurality of different phases with respect to said reference, and producing a display from said demodulated potentials.

7. The method of claim 6 wherein said step of sweeping comprises sweeping contrast of said visual pattern.

8. The method of claim 6 wherein said step of sweeping said visual parameter comprises sweeping the spatial frequency of said pattern, in cycles of the pattern per degree of visual arc of the observer.

9. The method of claim 7 or 8 further comprising varying the selected orientation of said pattern.

10. In a method for assessing visually-evoked response by varying a stimulus of a visual pattern presented to an observer and analyzing scalp potentials of said observer in response to said pattern; the improvement comprising sweeping a visual parameter of said pattern a plurality of times, each in a determined period, in a range which crosses an observer's visual threshold for said parameter, at least one of said sweeps starting below said visual threshold and at least another of said sweeps starting above said visual threshold, temporally modulating said pattern at a determined rate during said sweeping, synchronously demodulating said scalp potentials employing said determined rate of the temporal modulation as a reference, and producing a display from said demodulated scalp potentials, whereby the differences of thresholds of upwardly and downwardly swept visual parameter is a measure of adaptation of said observer.

11. The method of claim 10 wherein said step of sweeping comprises sweeping the contrast of said pattern.

12. The method of claim 10 wherein said step of sweeping comprises sweeping the frequency of said pattern in cycles per degree of visual arc of said observer.

13. In a method for assessing visually-evoked response wherein a variable visual pattern is presented to an observer and the scalp potentials of the observer responding to the stimulus of the variable visual patterns are analyzed; the process of selecting a low spatial frequency for the pattern of substantially 1 cycle/degree and sweeping a reversal rate thereof over an entire range of 1 to 50 reversal per second; observing a response peak at substantially 43 reversals per second; executing further testing with said reversal rate held constant at the value producing the observed response peak, with said spatial frequency remaining fixed at 1 cycle per degree; contrast threshold determinations made by sweeping contrast of said pattern constituting a non-invasive test which isolates the performance and integrity of the Y-type retinocortical pathways, whereby the oblique effect is abolished.

* * * * *